US008968652B2

(12) United States Patent
Ogihara

(10) Patent No.: US 8,968,652 B2
(45) Date of Patent: *Mar. 3, 2015

(54) OXYGENATOR

(75) Inventor: Mitsuaki Ogihara, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 830 days.

This patent is subject to a terminal disclaimer.

(21) Appl. No.: 13/208,932

(22) Filed: Aug. 12, 2011

(65) Prior Publication Data

US 2011/0300020 A1     Dec. 8, 2011

Related U.S. Application Data

(62) Division of application No. 11/654,599, filed on Jan. 18, 2007, now Pat. No. 8,017,075.

(30) Foreign Application Priority Data

Jan. 19, 2006 (JP) ................................. 2006-011702

(51) Int. Cl.
*A61M 1/00* (2006.01)
*A61M 37/00* (2006.01)
(Continued)

(52) U.S. Cl.
CPC .......... *A61M 1/1698* (2013.01); *A61M 1/3627* (2013.01); *A61M 2205/366* (2013.01); *A61M 2205/7527* (2013.01)
USPC .......................................... 422/45; 604/6.14

(58) Field of Classification Search
CPC ... A61M 1/1698; A61M 1/26; A61M 1/3626; A61M 1/3627; A61M 1/3666; A61M 3/3687; A61M 1/369; A61M 2001/10; A61M 2001/14; A61M 2001/16

USPC .............................. 422/44–48; 604/4.01–6.16
See application file for complete search history.

(56) References Cited

U.S. PATENT DOCUMENTS

| | | | |
|---|---|---|---|
| 3,807,958 | A | 4/1974 | Brumfield et al. |
| 4,183,961 | A | 1/1980 | Curtis |

(Continued)

FOREIGN PATENT DOCUMENTS

| | | |
|---|---|---|
| EP | 1 618 906 A1 | 1/2006 |
| JP | 7-328114 A | 12/1995 |

(Continued)

OTHER PUBLICATIONS

European Search Report issued by the European Patent Office in corresponding European Patent Application No. 07 00 0985, May 24, 2007, Munich DE.

(Continued)

*Primary Examiner* — Philip R Wiest
(74) *Attorney, Agent, or Firm* — Buchanan Ingersoll & Rooney PC

(57) ABSTRACT

An oxygenator that inhibits or prevents bubbles in blood from exiting through a blood outlet includes an oxygenator part which performs gas exchange on blood and a heat exchanging part which performs heat exchange on the blood. The oxygenators part has a housing that is generally in a rectangular parallelepiped form, with a hollow fiber membrane bundle positioned in the housing. The hollow fiber membrane bundle is formed by a multiplicity of hollow fiber membranes adapted to perform gas exchange. Blood flows along a blood passage comprised of gaps between the hollow fiber membranes and contacts the surface of the hollow fiber membranes where gas exchange occurs with gas flowing through the lumens of the hollow fiber membranes. In addition, a filter member is arranged on a downstream side of the hollow fiber membrane bundle so that bubbles present in the blood are caught by the filter member.

16 Claims, 4 Drawing Sheets

(51) Int. Cl.
*A61M 1/16* (2006.01)
*A61M 1/36* (2006.01)

(56) References Cited

U.S. PATENT DOCUMENTS

| | | | |
|---|---|---|---|
| 4,289,623 | A | 9/1981 | Lee |
| 5,034,188 | A | 7/1991 | Nakanishi et al. |
| 5,762,868 | A | 6/1998 | Leonard |
| 5,770,149 | A | 6/1998 | Raible |
| 6,503,451 | B2 | 1/2003 | Ikeda et al. |
| 6,723,283 | B2 | 4/2004 | Ghelli et al. |
| 6,730,267 | B2 | 5/2004 | Stringer et al. |
| 7,022,284 | B2 | 4/2006 | Brian et al. |
| 7,431,754 | B2 | 10/2008 | Ogihara et al. |
| 8,017,075 | B2 * | 9/2011 | Ogihara .................... 422/45 |
| 2006/0016743 | A1 * | 1/2006 | Ogihara et al. .......... 210/321.89 |
| 2007/0166190 | A1 | 7/2007 | Ogihara et al. |
| 2007/0231203 | A1 | 10/2007 | Mizoguchi et al. |

FOREIGN PATENT DOCUMENTS

| | | | | |
|---|---|---|---|---|
| JP | 2004-216448 | * | 6/2005 | ............. A61M 1/14 |
| WO | WO 97/16213 | A2 | 5/1997 | |
| WO | WO 00/06357 | A1 | 2/2000 | |

OTHER PUBLICATIONS

Communication pursuant to Article 94(3) EPC issued in corresponding European application.

* cited by examiner

OXYGENATOR

This application is a divisional of U.S. application Ser. No. 11/654,599 filed on Jan. 18, 2007, and claims priority to Japanese Application No. 2006-11702 filed on Jan. 19, 2006, the entire content of both of which is incorporated herein by reference.

TECHNICAL FIELD

The present invention generally relates to an oxygenator and a method performing gas exchange for blood.

BACKGROUND DISCUSSION

There are known oxygenators constructed to perform gas exchange by use of a multiplicity of hollow fiber membranes. An example of such an oxygenator is described in U.S. Pat. No. 6,503,451.

This oxygenator includes a housing, a hollow fiber membrane bundle received in the housing, blood-inlet and blood-outlet ports, and gas-inlet and gas-outlet ports so that gas exchange (i.e., oxygenation and carbon dioxide removal) is performed between blood and gas through the hollow fiber membranes.

In oxygenators constructed in this manner, bubbles may exist in the blood introduced through the blood inlet port. In such a case, bubbles are preferably removed by the hollow fiber membrane bundle.

However, the hollow fiber membrane bundle is specifically designed to efficiently carry out gas exchange, without being specifically intended to remove bubbles. Thus, there is a problem that bubbles are not fully removed by the hollow fiber membrane bundle, with the result that bubbles remaining in the blood that is discharged from the blood outlet port being carried downstream of the oxygenator. For this reason, a bubble-removing arterial filter is sometimes provided on an arterial line between the oxygenator and the patient.

SUMMARY

According to one aspect, a method of performing gas exchange for blood comprises: introducing blood into a blood inlet of a housing in which are positioned a plurality of hollow fiber membranes each having a lumen in communication with a gas inlet and a gas outlet so that the blood flows outside the lumens of the hollow fiber membranes toward a blood outlet; introducing gas into the lumens of the hollow fiber membranes to subject the blood flowing outside the lumens of the hollow fiber membranes to gas exchange; removing bubbles in the blood after the blood has been subjected to the gas exchange and before the blood is discharged form the housing by way of the blood outlet, with the removing of the bubbles occurring as a result of the blood which has been subjected to the gas exchange passing through a filter member which has a planar surface in direct contact with the hollow fiber membranes; and discharging the blood which has been subjected to the gas exchange and which has passed through the filter member from the housing by way of the blood outlet.

According to another aspect, a method of performing gas exchange for blood comprises: introducing blood into a blood inlet of a housing in which are positioned a plurality of hollow fiber membranes each having a lumen in communication with a gas inlet and a gas outlet so that the blood flows outside the lumens of the hollow fiber membranes toward a blood outlet; introducing gas into the lumens of the hollow fiber membranes to subject the blood flowing outside the lumens of the hollow fiber membranes to gas exchange; and catching bubbles in the blood after the blood has been subjected to the gas exchange and before the blood is discharged from the housing through the blood outlet, the bubbles being caught by virtue of the blood which has been subjected to the gas exchange passing through a bubble catching filter member. The bubbles caught by the bubble catching filter member enter the lumens of the hollow fiber membranes and are discharged out of the housing by way of the gas outlet, and the blood which has been subjected to the gas exchange and which has passed through the bubble catching filter member is discharged out of the housing by way of the blood outlet.

Another aspect involves a method of performing gas exchange for blood comprising Introducing blood into an inlet of a housing in which are positioned a plurality of hollow fiber membranes each having a lumen in communication with a gas inlet and a gas outlet so that the blood flows exteriorly of the hollow fiber membranes toward a blood outlet, introducing an gas into the lumens of the hollow fiber membranes to subject the blood flowing exteriorly of the hollow fiber membranes to gas exchange, discharging the blood which has been subjected to the gas exchange from the housing by way of the blood outlet, and removing bubbles in the blood in the housing before the blood is discharged from the housing by way of the blood outlet by passing the blood through a bubble filter.

BRIEF DESCRIPTION OF THE DRAWING FIGURES

DETAILED DESCRIPTION

Figure 1:
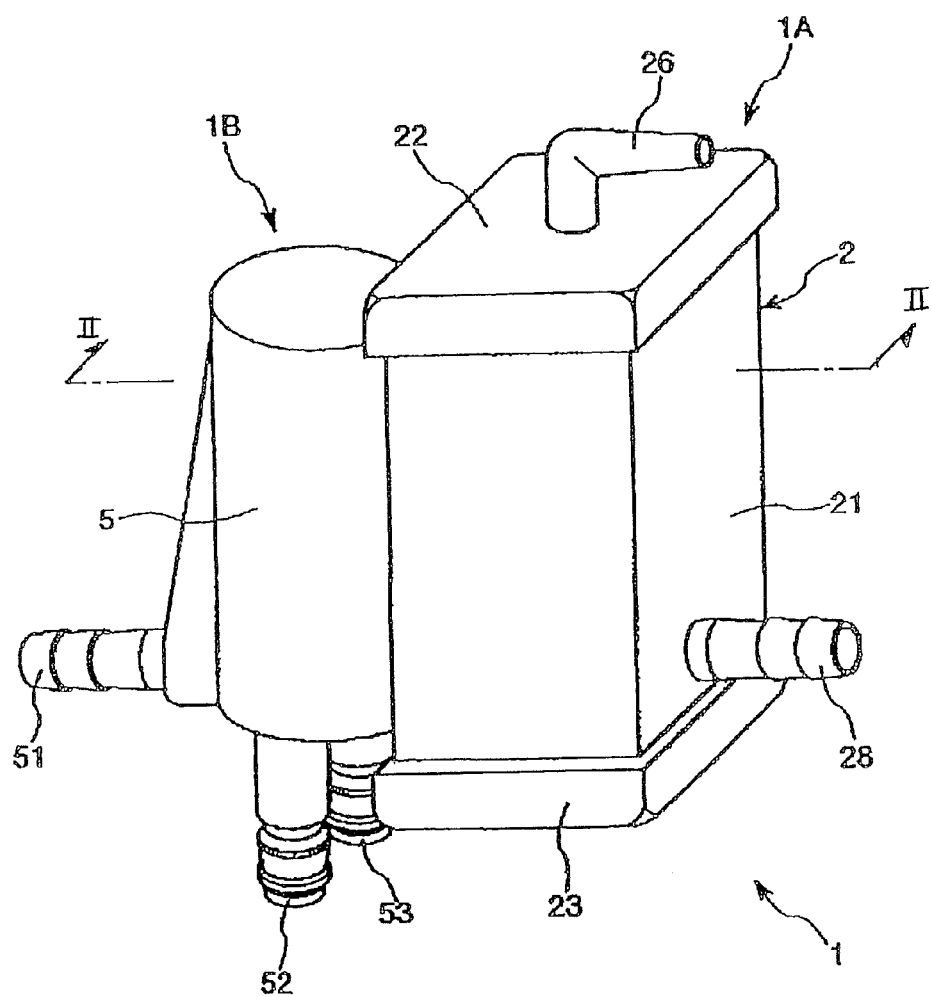
FIG. 1 is a perspective view of an embodiment of an oxygenator as disclosed herein.
Figure 2:
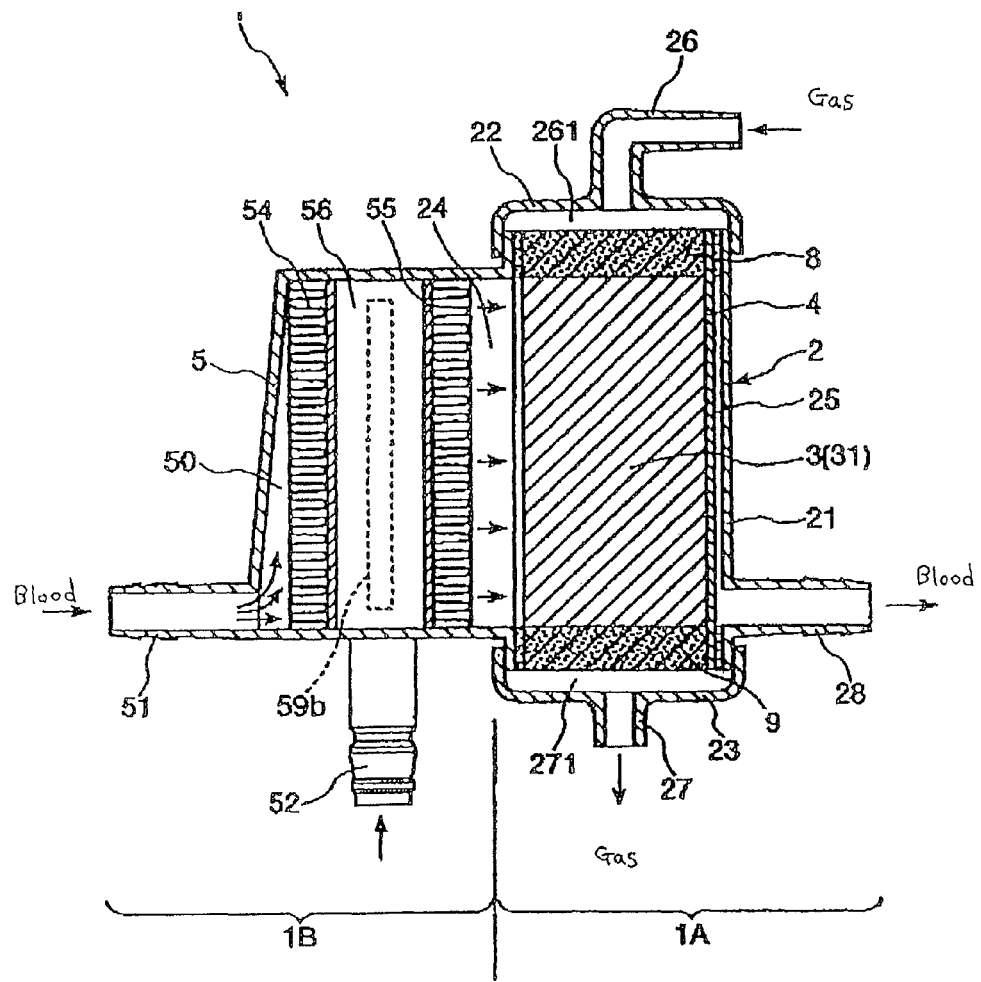
FIG. 2 is a cross-sectional side view of the oxygenator shown in FIG. 1 taken along the line II-II in FIG. 1.

The description below describes one embodiment of an oxygenator illustrated in the drawing figures. In FIGS. 1 and 2, the upper side is referred to as the "upper" side or "above", the lower side is referred to as the "lower" side or "below", the left side is referred to the "blood inlet side" or "upstream side", and the right side is referred to as the "blood outlet side" or "downstream side".

The illustrated version of the oxygenator 1 is a heat exchanger-equipped oxygenator comprising an oxygenating part 1A that performs gas exchange with the blood and a heat exchanging part (heat exchanger) 1B that performs heat exchange on the blood. By way of example, this oxygenator can be set up as a part of a blood extracorporeal circulation circuit.

The oxygenator 1 includes a housing 2 located on the side of the oxygenating part 1A, and a heat exchanger housing 5 located on the side of the heat exchanger 1B. The housings are preferably united or integrated together to form a single unitary body.

Describing initially various aspects of the oxygenating part 1A, the housing 2 is comprised of a cylindrical housing body 21. In the illustrated embodiment, the housing 2 is a rectangular parallelepiped form (inclusive of a substantially rectangular parallelepiped form) possessing a quadrilateral (rectangular or square) shape (hereinafter referred to as a "rectangular cylindrical housing body"), a first header or upper lid 22 closing the upper opening of the rectangular cylindrical housing body 21, and a second header (lower lid) 23 closing the lower opening of the rectangular cylindrical housing body 21. Both the first header 22 and second header 23 are a dish-shaped, including a plate-shaped portion with a projecting or upstanding wall extending around the periphery of the plate-shaped portion.

The rectangular cylindrical housing body 21, the first header 22 and the second header 23 are each formed of a resin material, for example polyolefin such as polyethylene or polypropylene, an ester resin (e.g., polyester such as polyethylene terephthalate or polybutylene terephthalate), a styrene resin (e.g., polystyrene, MS resin or MBS resin) or polycarbonate, a ceramics material of various kinds or a metal material. The first and second headers 22, 23 are secured in a liquid-tight manner to the rectangular cylindrical housing body 21 by, for example, joining by fusion or an adhesive.

The rectangular cylindrical housing body 21 is formed with a tubular blood outlet port 28 projecting in the lower region (lower half) of the blood outlet side. A tubular gas inlet port 26 projects from the upper surface of the first header 22. As shown in FIG. 2, a tubular gas outlet port 27 projects from the lower surface of the second header 23. The gas inlet port 26 has an intermediate portion bent nearly at a right angle so that the tip portion of the gas inlet port 27 is parallel to the blood outlet port 28.

A hollow fiber membrane bundle 3 is housed or received in the housing 2. The hollow fiber membrane bundle 3 is formed by integrating a multiplicity of hollow fiber membranes 31 serving for gas exchange and a filter member 4 serving for catching bubbles.

Figure 4:
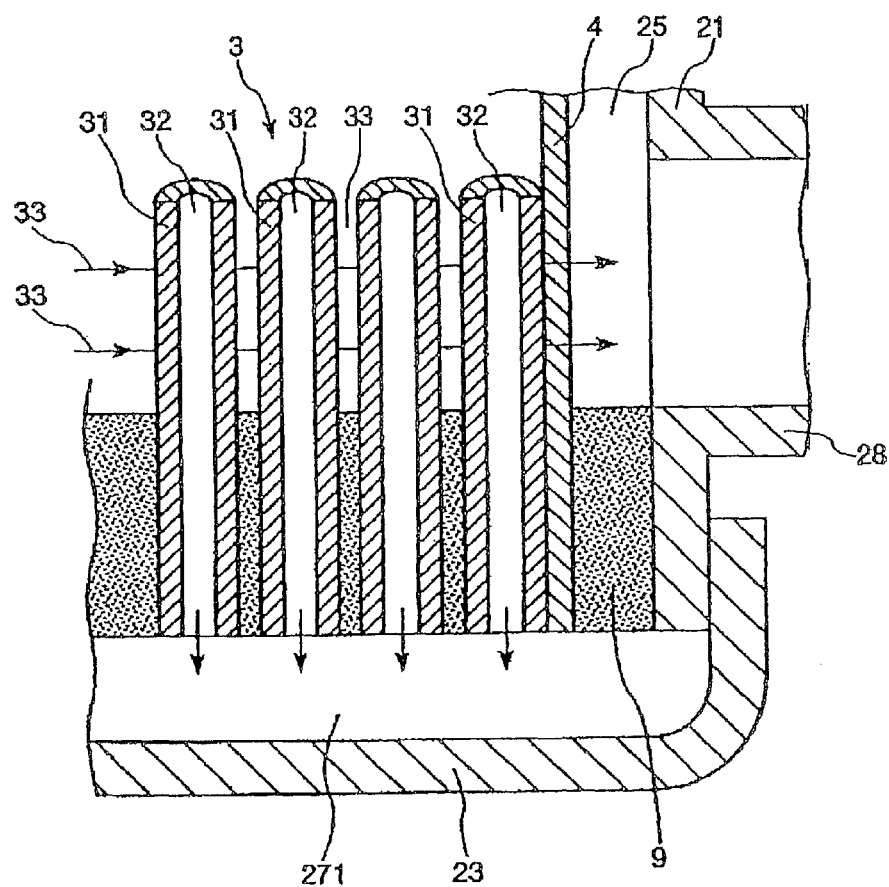
FIG. 4 is an enlarged cross-sectional view of a lower right region (fixing region of a hollow fiber membrane bundle and a filter member) of the oxygenator shown in FIG. 2.

As shown in FIG. 4, almost all the hollow fiber membranes 31 forming the hollow fiber membrane bundle 3 are arranged nearly parallel with one another. In this case, the hollow fiber membranes 31 are arranged vertically in the lengthwise direction.

The arrangement pattern, direction, etc. of the hollow fiber membranes 31 forming the hollow fiber membrane bundle 3 are not limited to those mentioned. For example, the hollow fiber membrane bundle 3 may be formed as a structure in which the hollow fiber membranes 31 are arranged horizontally, may be formed as a structure having points at which the hollow fiber membranes 31 obliquely intersect one another (intersections), may be formed as a structure in which all or part of the hollow fiber membranes 31 are arranged in a curved manner, or may be formed as a structure in which all or some of the hollow fiber membranes 31 are arranged in a corrugated, helical, spiral or annular manner.

The hollow fiber membranes 31 have opposite ends (upper and lower ends) fixed to the inner surfaces of the rectangular cylindrical housing body 21 by way of partitioning walls 8, 9 as shown in FIG. 2. The partitioning walls 8, 9 are formed of a potting material, e.g. polyurethane or silicone rubber.

Figure 3:
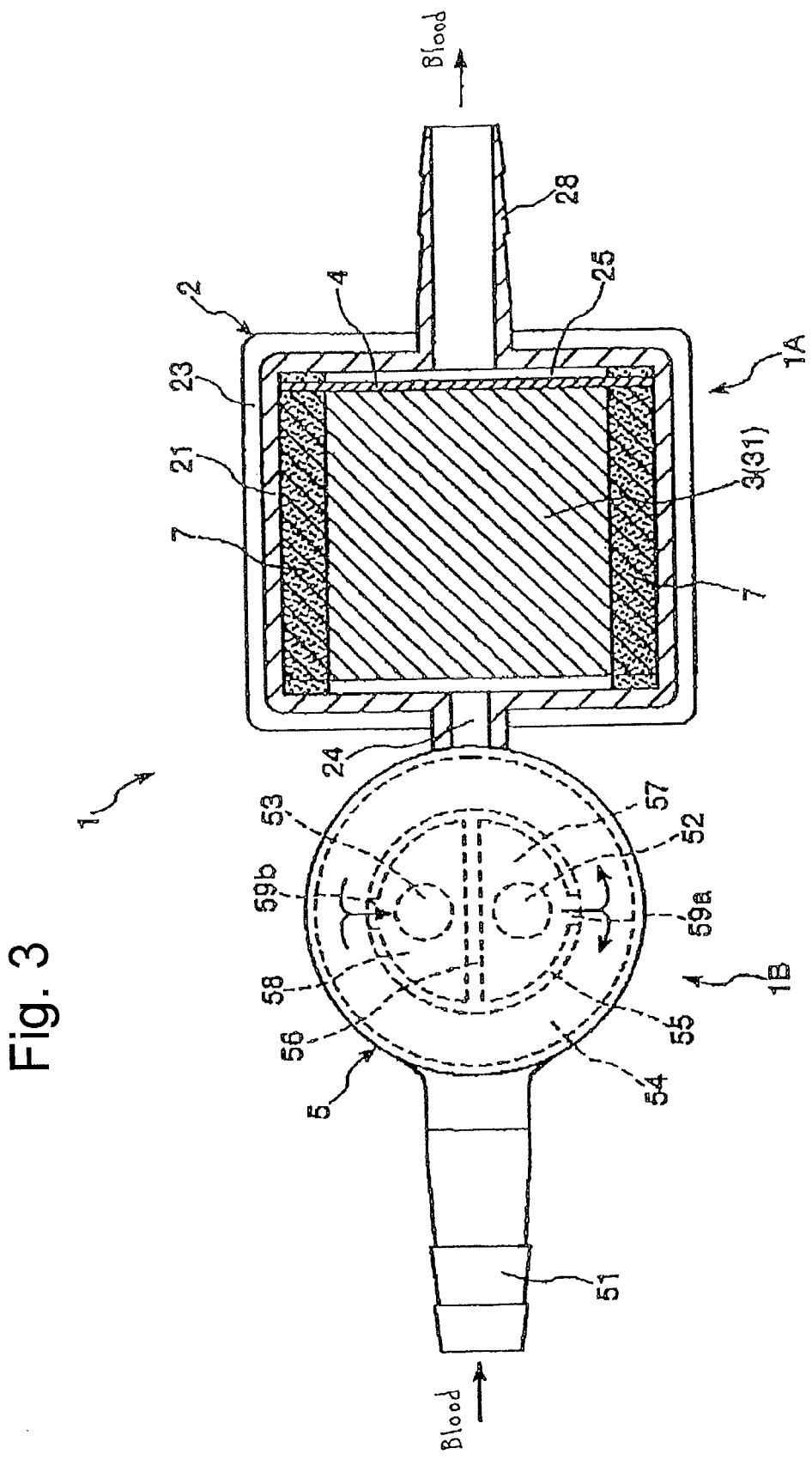
FIG. 3 is a top view, partially in cross-section, of the oxygenator shown in FIG. 1.

The hollow fiber membrane bundle 3 has widthwise opposite ends respectively fixed or secured to the inner surfaces of the rectangular cylindrical housing body 21 through a setting member 7 as illustrated in FIG. 3. The setting member 7 may be formed of a material similar to the material (potting material) forming the partitioning walls 8, 9 or of another material.

A gas inlet chamber 261 is defined by the first header 22 and one of the partitioning walls 8. Each of the hollow fiber membranes 31 possesses an upper opening that opens to and communicates with the gas inlet chamber 261. In addition, a gas outlet chamber 271 is defined by the second header 23 and the other partitioning wall 9. The hollow fiber membranes 31 each possess a lower opening that opens to and communicates with the gas outlet chamber 271. The hollow fiber membranes 31 each have a lumen extending between the open opposite ends forming a gas passage 32 through which gas (oxygen-containing gas) is adapted to flow. The gas inlet port 26 and the gas inlet chamber 261 constitute a gas inlet communicating with the gas passages 32 at an upstream end of the gas passages while the gas outlet port 27 and the gas outlet chamber 271 constitute a gas outlet communicating with the gas passages 32 at a downstream end of the gas passages.

The hollow fiber membrane bundle 3 is sized to nearly completely fill the interior of the rectangular cylindrical housing body 21 so that the hollow fiber membrane bundle 3 takes a rectangular parallelepiped form (inclusive of a substantially rectangular parallelepiped form). Due to this, a relatively high charge efficiency by the hollow fiber membranes 31 is available (with less dead space) in the rectangular cylindrical housing body 21 of similar form, which contributes to the size reduction and performance improvement of the oxygenating part 1A.

The hollow fiber membranes 31 are exposed between the partitioning walls 8, 9 within the housing 2. A blood passage 33 is formed exterior of the hollow fiber membranes 31, i.e., at gaps between the hollow fiber membranes 31, allowing blood to flow from left to right in FIG. 2.

A blood inlet aperture (blood inlet space) 24 forms a blood inlet possessing a strip or elongated form extending vertically (nearly parallel with the arrangement of the hollow fiber membranes 31) at an upstream end of the blood passage 33 (closer to an upstream surface of the hollow fiber membrane bundle 3), i.e., in a connection region between the rectangular cylindrical housing body 21 and the heat exchanger housing 5. The housing 2 has an interior in communication with the interior of the heat exchanger housing 5 through the blood inlet aperture 24. This structure allows for relatively efficient transfer of blood from the heat exchanging part 1B to the oxygenating part 1A.

The blood inlet aperture 24 preferably has a length (vertical length as seen with reference to FIG. 2) equal to or greater than 70% of the effective length of the hollow fiber membrane 31 (i.e., the length between the lower face of the partitioning wall 8 and the upper face of the partitioning wall 9), with the length of the blood inlet aperture 24 preferably being no greater than the effective length of the hollow fiber membrane 31. In the illustrated embodiment, the length of the blood inlet aperture 24 is equal to the effective length of the hollow fiber membrane 31. This disclosed length of the blood inlet aperture 24 allows for relatively efficient transfer of blood from the heat exchanging part 1B to the oxygenating part 1A and for gas exchange of blood in the blood passage 33.

At least in the upstream end of the blood passage 33 (closer to the blood inlet aperture 24), the flow of blood is in a direction nearly orthogonal to the lengthwise extent or direction of the hollow fiber membranes 31. This also helps contribute to a relatively efficient gas exchange of the blood flowing along the blood passage 33.

At the downstream end of the blood passage 33 (closer to the downstream surface of the hollow fiber membrane bundle 3), a gap is formed between a filter member 4, described in more detail later, and an inner surface of the rectangular cylindrical housing body 21. The gap forms a blood outlet aperture (blood outlet space) 25. The blood outlet aperture 25A communicates with the blood outlet port 28, with the blood outlet aperture 25 and blood outlet port 28 forming a blood outlet. The blood outlet aperture 25 provides the blood outlet with a space where the blood transmitted through the filter member 4 is to flow toward the blood outlet port 28, thus discharging the blood relatively smoothly.

The hollow fiber membrane bundle 3, the filter member 4 and the blood passage 33 are positioned between the blood inlet aperture 24 and the blood outlet aperture 25.

By way of example, the hollow fiber membranes 31 can be fabricated of porous gas-exchange membranes. The porous hollow fiber membranes can be configured to possess an inner diameter of approximately 100-1000 µm, a wall thickness of approximately 5-200 µm, preferably 10-100 µm, a porosity of approximately 20-80%, preferably approximately 30-60%, and a pore size of approximately 0.01-5 µm, preferably approximately 0.01-1 µm.

The hollow fiber membrane 31 is preferably fabricated of a hydrophobic polymer material, e.g. polypropylene, polyethylene, polysulfone, polyacrylonitrile, polytetrafluoroethylene or polymethyl pentane. Polyolefin resin is preferred, and polypropylene is more preferred. Pores are preferably formed in a wall of the material by, for example, stretching or solid-liquid phase separation.

The hollow fiber membranes 31 of the hollow fiber membrane bundle 3 have a length (effective length) that is not particularly limited, but is preferably approximately 30-150 mm, more preferably approximately 50-100 mm.

The hollow fiber membrane bundle 3 has a thickness (horizontal length in FIG. 2) that is not particularly limited, but is preferably approximately 10-100 mm, more preferably approximately 20-80 mm.

Similarly, the width (vertical length in FIG. 3) of the hollow fiber membrane bundle 3 is not particularly limited, but is preferably approximately10-100 mm, more preferably approximately 20-80 mm.

The filter member 4 is provided at a position downstream of the hollow fiber membrane bundle 3 (closer to the blood outlet) to thus catch bubbles in the blood flowing along the blood passage 33. The filter member 4 can be formed as a flat sheet member nearly in a rectangular form (hereinafter referred to as a "sheet"). The filter member 4 is fixed in the housing 2 by being secured at its edges (four sides) through the partitioning walls 8, 9 and the respective setting members 7.

The filter member 4 is positioned so that its one surface is in contact with the downstream surface (closer to the blood outlet portion) of the hollow fiber membrane bundle 3, thus covering nearly all the downstream surface. The filter member 4 thus has an increased effective area to thereby make it possible to relatively fully exhibit the capability of catching bubbles. Also, by increasing the effective area of the filter member 4, even if clogging (e.g., adhesion of blood aggregates) occurs in a part of the filter member 4, blood flow is not completely obstructed.

The filter member 4 may be, for example, in a mesh form, or of a woven fabric, a non-woven fabric or a combination thereof. Of these, the mesh form is preferred, with a screen filter being particularly preferred. This makes it possible to capture or stop bubbles more positively while permitting the passage of blood more easily.

When the filter member 4 is in the form of a mesh, the mesh size is not limited, though is usually preferably 80 µm or smaller, more preferably approximately 15-60 µm, further preferably 20-45 µm. This makes it possible to catch comparatively fine bubbles without increasing the passage resistance to blood, thus providing a relatively high catch efficiency of bubbles (bubble removal capability).

The material from which the filter member 4 is made can be, for example, polyolefin such as polyamide, polyethylene or polypropylene, polyester such as polyethylene terephthalate, polybutylene terephthalate, nylon, cellulose, polyurethane, or an aramid fiber. A particularly preferred material is polyethylene terephthalate, polyethylene or polyurethane due to the relatively excellent resistance to blood clotting and the capability of being less clogged.

The filter member 4 also preferably possesses hydrophilicity. Namely, the filter member 4 preferably is made itself of a hydrophilic material or has been subjected to a hydrophilizing processing (e.g. plasma processing). This makes it relatively easy to remove bubbles upon priming the oxygenator 1. Also, when the blood mixed with bubbles passes through, it is difficult for the bubbles to pass through, thus improving the bubble removal capability of the filter member 4 and positively preventing the bubbles from passing out of the blood outlet port 28.

The filter member 4 may be comprised of one sheet (particularly one in a mesh form, like a screen filter) or two or more sheets.

As described above, a gap (i.e., blood outlet aperture 25) exists between the filter member 4 and the housing 2 as seen in FIGS. 2 and 3. This helps prevent the filter member 4 from coming into direct or close contact with the inner surface of the housing 2. The blood passing the filter member 4 is allowed to relatively easily and smoothly flow down the blood outlet aperture 25 and then to the blood outlet port 28.

The filter member 4 is rectangular (or square) in plan in the illustrated embodiment. However, the plan form of the filter member 4 is not limited to such shape and may instead be trapezoidal, parallelogram, elliptic or oval, for example.

By arranging the filter member 4 in the described manner, even when bubbles exist in the blood flowing along the blood passage 33, such bubbles can be caught, thereby preventing the bubbles from going out of the blood outlet port 28. This eliminates the necessity of an arterial filter conventionally provided on the arterial line.

The bubbles, caught by the filter member 4, stay on the upstream side of the filter member 4 where they are able to pass into the lumens (gas passages 32) of the hollow fiber membranes 31 through the multiplicity of fine pores formed in the wall of the hollow fiber membranes 31 where they are discharged at the gas outlet port 27, together with the gas flowing the gas passage 32. This eliminates the need for an arterial filter, thus reducing the priming time upon start of using the oxygenator and preventing the adverse effect caused due to the bubbles staying in the blood passage 33 (e.g. lowered gas-exchange capability of the hollow fiber membrane bundle 3).

The heat exchanger 1B comprises a heat exchanger housing 5. The heat exchanger housing 5 is nearly in a cylindrical form having upper and lower closed ends. The interior of the heat exchanger housing 5 forms a blood chamber 50. The heat exchanger housing 5 is formed with a tubular heating medium inlet port 52 and a heating medium outlet port 53, both of which project from the lower end (lower surface) of the heat exchanger housing 5. Meanwhile, a tubular blood inlet port 51 projects in the lower portion (lower left region in FIG. 2) of the heat exchanger housing 5. The blood inlet port 51 has a lumen communicating with the blood chamber 50.

Arranged in the interior of the heat exchanger housing 5 is a heat exchange element 54 that is wholly cylindrical in form, a heating medium chamber-forming member (cylindrical wall) 55 possessing a cylindrical form and provided along the inner periphery of the heat exchange element 54, and a partitioning wall 56 separating the inner space of the heating medium chamber-forming member 55 into an inlet heating medium chamber 57 and an outlet heating medium chamber 58. The heating medium chamber-forming member 55 forms a heating medium chamber that temporarily stores the heating medium at the inside of the heat exchange element 54 and helps prevent the cylindrical heat exchange element from deforming.

The heating medium chamber-forming member 55 and the partitioning wall 56 are fixed in the heat exchanger housing 5 by joining, for example by fusion or an adhesive. The heating medium chamber-forming member 55 and the partitioning wall 56 may be formed as separate members or as a one-piece single unitary body.

The heating medium chamber-forming member 55 is provided with vertically extending strip-formed openings 59a, 59b that penetrate the wall of the heating medium chamber-forming member 55. The openings 59a, 59b are arranged at diametrically opposite positions on opposite sides of the partitioning wall 56 as shown in FIG. 3. The opening 59a communicates with the inlet heating medium chamber 57 while the opening 59b communicates with the outlet heating medium chamber 58.

In the illustrated version, the heat exchange element 54 is in the form of a so-called bellows-type heat exchange element (bellows tube) as shown in FIG. 2. The bellows-type heat exchange element 54 comprises a bellows-formed central portion and a cylindrical portion at each end (upper and lower ends). The bellows-formed central portion is comprised of a multiplicity of hollow annular projections that are parallel (inclusive of nearly parallel) to one another so as to form a plurality of closely arranged undulations. The inner diameter of each cylindrical end portion is equal to (inclusive of nearly equal to) the inner diameter of the bellows-formed central portion. The heat exchange element 54 is formed of a metal material such as stainless steel or aluminum, or a resin material such as polyethylene or polycarbonate, for example. It is preferable to use a metal material, such as stainless steel or aluminum for reasons of strength and heat exchange efficiency. It is particularly preferable to construct the heat exchange element 54 as a metal-made bellows tube in a corrugated form having a multiplicity of repetitive concavo-convex portions nearly orthogonal to the axis of the heat exchange element 54.

The heat exchanger housing 5, the heating medium chamber-forming member 55 and the partitioning wall 56 are of a material, e.g. polyolefin such as polyethylene or polypropylene, an ester resin (e.g. polyester such as polyethylene terephthalate or polybutylene terephthalate), a styrene resin (e.g. polystyrene, MS resin or MBS resin), a resin material such as polycarbonate, a ceramics material of various kinds or a metal material.

Referring to FIGS. 1 to 3, set forth below is a description of the flow of heating medium in the heat exchanging part 1B of the oxygenator 1. The heating medium passing through the heating medium inlet port 52 first flows into the inlet heating medium chamber 57 and then to the outer peripheral side of the heating medium chamber-forming member 55 via the opening 59a, thus spreading over the entire periphery of the heating medium-chamber forming member 55 and going into a multiplicity of recesses of the bellows (to the inside of hollow annular projections) of the heat exchange element 54. This heats up or cools down the heat exchange element 54 in contact with the heating medium. Thus, heat exchange (heating or cooling) is effected with the blood flowing at the outer peripheral side of the heat exchange element 54.

The heating medium, served for heating or cooling the heat exchange element 54, enters the outlet heating medium chamber 58 through the opening 59b and then exits at the heating medium outlet port 53.

Although the oxygenator described above and illustrated in the drawing figures includes the heat exchanging part 1B, it is to be understood that the heat exchanger part 1B is not required, and the oxygenator part 1A can be used independently of the heat exchanger part 1B.

Referring to FIGS. 1 to 4, the following is a description of the blood flow in the oxygenator 1 of this embodiment.

In the oxygenator 1, the blood coming through the blood inlet port 51, flows into the blood chamber 50, i.e. between the inner peripheral surface of the heat exchanger housing 5 and the heat exchange element 54, where it contacts the outer surface of the plurality of hollow annular projections of the heat exchange member 54, thus effecting heat exchange (heating or cooling). The blood thus heat exchanged gathers at a downstream portion of the blood chamber 50 and then flows into the housing 2 of the oxygenating part 1A through the blood inlet aperture 24.

The blood passing through the blood inlet aperture 24 flows downstream along the blood passage 33 formed in the gaps between the hollow fiber membranes 31. Meanwhile, the gas (gas containing oxygen), supplied through the gas inlet port 26 is distributed by the gas inlet chamber 261 into the gas passages 32, i.e., the lumens of the hollow fiber membranes 31. After passing through the gas passages 32, the gas is collected in the gas outlet chamber 271 and allowed to exit at the gas outlet port 27. The blood, flowing along the blood passage 33 contacts the surfaces of the hollow fiber membranes 31 so that gas exchange (oxygenation, and carbon dioxide removal) can be carried out with the gas flowing through the gas passages 32.

In the event bubbles are present in the gas-exchanged blood, the bubbles are caught by the filter member 4 and not allowed to flow downstream of the filter member 4. The bubbles caught at the filter member 4 gather or are stopped at the upstream side of the filter member 4 where they enter the lumens (gas passages 32) of the hollow fiber membranes 31 via the multiplicity of fine pores formed in the wall of the hollow fiber membranes 31. The bubbles are then discharged at the gas outlet port 27 together with the gas flowing through the gas passage 32.

The blood thus subjected to gas exchange and bubble removal flows into the blood outlet aperture 25 where it flows down the blood outlet aperture 25 and exits at the blood outlet port 28.

In the oxygenator 1 of this embodiment, it is preferable to make the surfaces contacted with blood (e.g., the inner surface of the housing 2, the inner surface of the heat exchanger housing 5, the surface of the heating medium chamber-forming member 55, the surface of the partitioning wall 56, the setting member 7, and the surfaces of the partitioning walls 8, 9 facing the blood passage 33) antithrombotic. The antithrombotic surface can be formed by coating and fixing an antithrombotic material over the surface. The antithrombotic material includes heparin, urokinase, HEMA-St-HEMA copolymer, poly-HEMA and so on.

In the oxygenator 1, the flow rate of blood through the blood inlet port 51 is not especially limited because it is different depending upon patient's physique and operation scheme. However, usually, some 0.1-2.0 L/min is preferred in infant or child, some 2.0-5.0 L/min is preferred in child in elementary or middle school, and some 3.0-7.0 L/min is preferred in adult.

In the oxygenator 1, the flow rate of the gas supplied through the gas inlet port 26 is not especially limited because it may differ or vary depending upon, for example, a patient's physique and operation scheme. However, usually, 0.05-4.0 L/min is a preferred gas flow rate in infants or younger children, while 1.0-10.0 L/min is a preferred gas flow rate for children in elementary or middle school, and 1.5-14.0 L/min is a preferred gas flow rate for adults.

The oxygen concentration in the gas supplied through the gas inlet port 26 is also not particularly limited because it is different depending upon the metabolic amount of oxygen/carbon-dioxide gas of a patient under operation. However, an example is 40-100%.

The maximum continuous operation time of the oxygenator 1 is not limited to a specific time because it may differ depending upon, for example, the patient's condition and operation scheme. However, a usual time is approximately 2-6 hours. The maximum continuous operation time of the oxygenator 1 will rarely amount to a time as long as nearly 10 hours.

The oxygenator illustrated and described here is not limited to all of the specific features and details described above and illustrated in the drawing figures as various features and elements constituting the oxygenator can be replaced with others that are generally suited to exhibiting similar operations or functions.

For example, different structures from those illustrated can be applied to the structure or form of the connection between the housing 2 and the heat exchanger housing 5, the position and projecting direction of the gas inlet port 26, the gas outlet port 27, the blood outlet port 28, etc. into and out of the housing 2, and the position and projecting direction of the blood inlet port 51, the heating medium inlet port 52 and the heating medium outlet port 53 into and out of the heat exchanger housing 5. Similarly, the position of the oxygenator 1 in use (positional relationship of various elements relative to the vertical direction) is not limited to that illustrated.

Thus, it is to be recognized that the principles, preferred embodiment(s) and modes of operation have been described in the foregoing specification, but the invention which is intended to be protected is not to be construed as limited to the particular embodiment(s) disclosed. Further, the embodiment(s) described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method of performing gas exchange for blood comprising:
    introducing blood into a blood inlet of a housing in which are positioned a plurality of hollow fiber membranes each having a lumen in communication with a gas inlet and a gas outlet so that the blood flows outside the lumens of the hollow fiber membranes toward a blood outlet;
    introducing gas into the lumens of the hollow fiber membranes to subject the blood flowing outside the lumens of the hollow fiber membranes to gas exchange;
    removing bubbles in the blood after the blood has been subjected to the gas exchange and before the blood is discharged from the housing by way of the blood outlet, the removing of the bubbles occurring as a result of the blood which has been subjected to the gas exchange passing through a filter member which has a planar surface in direct contact with the hollow fiber membranes; and
    discharging the blood which has been subjected to the gas exchange and which has passed through the filter member from the housing by way of the blood outlet.

2. The method according to claim 1, wherein the blood which has passed through the filter member flows through a gap between the filter member and an inner surface of the housing before being discharged from the housing by way of the blood outlet.

3. The method according to claim 1, further comprising introducing the blood into a heat exchanger, and discharging the blood from the heat exchanger before introducing the blood into the blood inlet.

4. The method according to claim 1, further comprising passing the blood through a heat exchanger before introducing blood into the blood inlet.

5. A method of performing gas exchange for blood comprising:
    introducing blood into a blood inlet of a rectangular shape housing in which are positioned a plurality of hollow fiber membranes each having a lumen in communication with a gas inlet and a gas outlet so that the blood flows outside the lumens of the hollow fiber membranes toward a blood outlet;
    introducing gas into the lumens of the hollow fiber membranes to subject the blood flowing outside the lumens of the hollow fiber membranes to gas exchange;
    catching bubbles in the blood after the blood has been subjected to the gas exchange and before the blood is discharged from the housing through the blood outlet, the bubbles being caught by virtue of the blood which has been subjected to the gas exchange passing through a bubble catching filter member;
    the bubbles caught by the bubble catching filter member entering the lumens of the hollow fiber membranes and being discharged out of the housing by way of the gas outlet; and
    discharging the blood which has been subjected to the gas exchange and which has passed through the bubble catching filter member out of the housing by way of the blood outlet.

6. The method according to claim 5, wherein the blood which has passed through the filter member flows through a gap between the filter member and an inner surface of the housing before being discharged from the housing by way of the blood outlet.

7. The method according to claim 5, further comprising introducing the blood into a heat exchanger, and discharging the blood from the heat exchanger before introducing the blood into the blood inlet.

8. The method according to claim 5, further comprising passing the blood through a heat exchanger before introducing blood into the blood inlet.

9. The method according to claim 5, wherein the bubble catching filter member through which the blood passes is in direct contact with the hollow fiber membranes.

10. The method according to claim 5, wherein the bubble catching filter member through which the blood passes has a planar surface in direct contact with the hollow fiber membranes.

11. A method of performing gas exchange for blood comprising:
    introducing blood into an inlet of a rectangular shape housing in which are positioned a plurality of hollow fiber membranes each having a lumen in communication with a gas inlet and a gas outlet so that the blood flows exteriorly of the hollow fiber membranes toward a blood outlet;
    introducing gas into the lumens of the hollow fiber membranes to subject the blood flowing exteriorly of the hollow fiber membranes to gas exchange;

discharging the blood which has been subjected to the gas exchange from the housing by way of the blood outlet; and removing bubbles in the blood in the housing after the blood has been subjected to the gas exchange and before the blood is discharged from the housing by way of the blood outlet.

12. The method according to claim 11, wherein the bubbles are removed by passing the blood which has been subjected to the gas exchange through a bubble filter.

13. The method according to claim 12, wherein the blood which has passed through the bubble filter flows through a gap between the bubble filter and an inner surface of the housing before being discharged from the housing by way of the blood outlet.

14. The method according to claim 11, further comprising introducing the blood into a heat exchanger, and discharging the blood from the heat exchanger before introducing the blood into the blood inlet.

15. The method according to claim 11, further comprising passing the blood through a heat exchanger before introducing blood into the blood inlet of the housing.

16. The method according to claim 11, further comprising discharging the bubbles which have been removed from the blood out of the housing by conveying the bubbles through the lumens of the hollow fiber membranes and through the gas outlet.

\* \* \* \* \*